United States Patent [19]

Otagiri et al.

[11] Patent Number: 5,317,026
[45] Date of Patent: May 31, 1994

[54] ACETAMIDE DERIVATIVE AND APPLICATION THEREOF

[75] Inventors: Masaki Otagiri; Teruko Imai, both of Kumamoto, Japan

[73] Assignee: Snow Brand Milk Products Co., Ltd., Hokkaido, Japan

[21] Appl. No.: 25,167

[22] Filed: Mar. 2, 1993

[30] Foreign Application Priority Data

Mar. 4, 1992 [JP] Japan .................................. 4-082864

[51] Int. Cl.$^5$ ................... A61K 31/445; C07D 211/32
[52] U.S. Cl. .................................... 514/331; 546/233; 546/234
[58] Field of Search ................. 546/233, 234; 514/331

[56] References Cited

U.S. PATENT DOCUMENTS

| | | | |
|---|---|---|---|
| 4,293,557 | 10/1981 | Shibata et al. | 424/267 |
| 4,302,472 | 11/1981 | Cozzi et al. | 424/324 |
| 4,837,316 | 6/1989 | Sekine et al. | 546/214 |
| 4,988,705 | 1/1991 | Ganguly et al. | 514/282 |
| 4,988,828 | 1/1991 | Kashiwaba et al. | 549/496 |
| 5,106,851 | 4/1992 | Turconi et al. | 514/259 |
| 5,126,352 | 6/1992 | Ganguly et al. | 514/293 |
| 5,159,085 | 10/1992 | Failli et al. | 548/310.1 |
| 5,192,774 | 3/1993 | Shinozaki et al. | 514/315 |

FOREIGN PATENT DOCUMENTS 58-15944 1/1983 Japan .
58-15945 1/1983 Japan .

Primary Examiner—C. Warren Ivy
Assistant Examiner—Celia Chang
Attorney, Agent, or Firm—Testa, Hurwitz & Thibeault

[57] ABSTRACT

2-Substituted-N-{3-[3-(1-piperidinomethyl)phenoxy]-propyl}acetamide, derivatives thereof, and pharmaceutically acceptable salts thereof. The substitution group may be aminomethylcyclohexane carbonyl group or N-carbobenzoxy-p-aminomethylhexane carbonyl group. The compounds having the first-mentioned group can be an effective component of an antiulcer drug composition, and the compounds of the last-mentioned group are intermediates for producing the compounds having the first-mentioned group. Disclosed also is an antiulcer drug composition comprising the above compound as an effective component. The antiulcer drug composition exhibits both the gastric acid secretion inhibitive activity and the gastric mucosa protective activity, and is effective as suppression and cure of ulcers.

16 Claims, 6 Drawing Sheets

ACETAMIDE DERIVATIVE AND APPLICATION THEREOF

BACKGROUND OF THE INVENTION

1. Field of the Invention

The present invention relates to a novel compound, 2-substituted-N-{3-[3-(1-piperidinomethyl)phenoxy]-propyl}acetamide, derivatives thereof, and pharmaceutically acceptable salts thereof. The present invention also relates to a drug composition, especially to an antiulcer drug composition, comprising said compound as an effective component.

2. Description of the Background Art

Ulcers, typified by stress ulcer, are diseases characteristic to modern human beings. Their increase in the future is anticipated. For example, in the case of stress ulcer, depression of gastrointestinal tract movement, degradation of gastrointestinal tract vascular flow, and the like are reported to be caused by the action of the adrenocorticotropic hormones releasing factor which is induced by hypothalamus irritation. Simultaneous actions of parasympathetic nerves and sympathetic nerves render the conditions even more complicated. In the case of peptic ulcer, the ulcer is considered to develop when a balance between aggressive factors, such as pepsin, gastric acid, or the like, and defensive factors, such as mucus, mucosal vascular flow, or the like, is lost. Thus, an ulcer is caused by various reasons, including abnormal secretion of gastric acid, hormones, and the like; inhibition in the synthesis of mucus; inhibition in the synthesis of prostaglandin; and the like. Ulcers are thus considered to be formed due to coincidence of various factors.

On the other hand, in any types of ulcers, reducing gastric acid secretion, accelerating synthesis of muco polysaccharide which consists of gastric mucus, or increasing gastric mucosal vascular flow are believed to alleviate deep pains caused by ulcers and to degenerate the ulcers.

Nowadays, roughly classified, two types of antiulcer drugs are on sale; one is Histamine H₂-antagonist which has an action to depress gastric acid secretion, and the other is a gastric mucosa protective agent which exhibits actions to protect gastric mucosa. Although histamine H₂-antagonist shows a superior action and exhibits its effect rapidly, it has a problem that the rebound phenomenon is caused by repeated administration. The gastric mucosa protective agent, on the other hand, exhibits only a weak action, and, depending on the circumstances, it takes a long period of time for the agent to exhibit the its effect.

In view of the above-mentioned drawbacks in conventional antiulcer drugs, the present inventors have synthesized a number of compounds in order to develop a new antiulcer drug and were successful in obtaining a novel compound possessing both the gastric acid secretion inhibitive activity and the gastric mucosa protective activity.

Accordingly, an object of the present invention is to provide a novel compound which can exhibit both the gastric acid secretion inhibitive activity and the gastric mucosa protective activity, and which can be used as an effective component for a new type of antiulcer drug.

Another object of the present invention is to provide a drug, particularly an antiulcer drug, comprising said novel compound as an effective component.

Still another object of the present invention is to provide an intermediate compound for preparing said novel compound.

The present inventors have synthesized a number of compounds for the purpose of obtaining a novel compound possessing both of the above-mentioned activities, and found that 2-substituted-N-{3-[3-(1-piperidinomethyl)phenoxy]propyl}acetamide exhibits both the gastric acid secretion inhibitive activity and the gastric mucosa protective activity.

SUMMARY OF THE INVENTION

The above object can be resolved according to the present invention by the provision of novel compounds, 2-substituted-N-{3-[3-(1-piperidinomethyl)phenoxy]-propyl}acetamide, represented by the following formula,

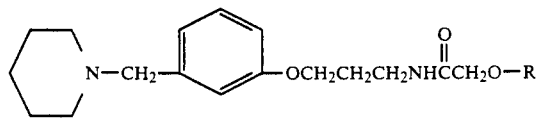

wherein R is an aminomethylcyclohexane carbonyl group,

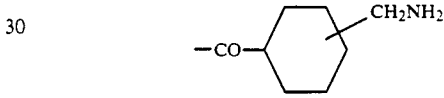

or an N-carbobenzoxy-aminomethylhexane carbonyl group,

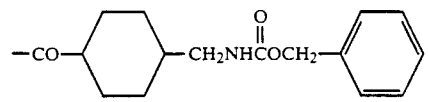

derivatives thereof, and pharmaceutically acceptable salts thereof.

Among the above compounds, acetamide compounds having the first-mentioned group, i.e., aminomethylcyclohexane carbonyl group, are compounds exhibiting both of the aforementioned actions, and the compounds of the last-mentioned group, i.e., N-carbobenzoxy-aminomethylhexane carbonyl group, are intermediates for producing the compounds having the first-mentioned group.

Among the compounds represented by the above formula, the following compounds are particularly noted.

2-(aminomethylcyclohexanecarboxy)-N-{3-[3-(1piperidinomethyl)phenoxy]propyl}acetamide,

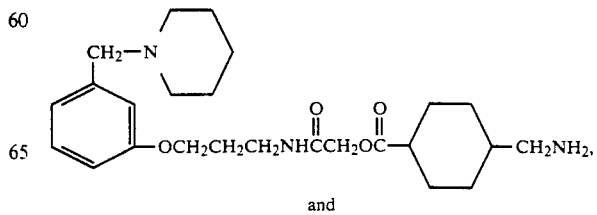

and 2-(N-carbobenzoxy-trans-p-aminomethylhexanecarboxy)-N-{3-[3-(1-piperidinomethyl)phenoxy]propyl}acetamide,

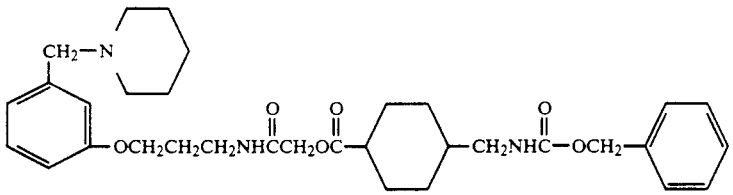

The above object the present invention is further resolved by the provision of a drug composition, particularly, an antiulcer drug composition, comprising one or more of the above-described compounds or a derivative thereof as an effective component. Derivatives of the present invention include compounds with the terminal amino group, piperidino group, or the like substituted by other groups.

The compounds of the present invention may be present as cys or trans stereoisomers and may form a pharmaceutically acceptable salt with an acid such as hydrochloric acid, citric acid, maleic acid, or the like. Thus, the compounds of the present invention include such stereoisomers and pharmaceutically acceptable salts.

The above object is still further resolved according to the present invention by the use of the compounds of the last-mentioned group, i.e., N-carbobenzoxy-aminomethylhexane carbonyl group, as an intermediate for producing the compounds having the first-mentioned group, i.e., aminomethylcyclohexane carbonyl group.

Other and further objects, features and advantages of the present invention will appear more fully from the following description.

DETAILED DESCRIPTION OF THE INVENTION AND PREFERRED EMBODIMENTS

There are various methods of preparing the compounds of the present invention. The following methods are preferred from the aspect of both the yield and the easiness.

First, 3-piperidinomethylphenol is synthesized from 3-hydroxybenzaldehyde and piperidine. The 3-piperidinomethylphenol is then reacted with 3-chloropropylamine to produce N-[3-(3-aminopropoxy)benzyl]piperidine, which is reacted with acetoxyacetyl chloride to obtain N-[3-(3-piperidinomethylphenoxy)-propyl]hydroxyacetamide. Separately, tranexamic acid and carbobenzoxy chloride are reacted to produce N-carbobenzoxyaminomethylhexanecarboxy chloride. The two compounds thus obtained are then reacted first to afford N-{3-[3-(1-piperidinomethyl)phenoxy]-propyl}-2-(N-carbobenzoxy-aminomethylhexanecarboxy)acetamide. This compound is then reduced into 2-(aminomethylcyclohexanecarboxy)-N-(3-[3-(piperidinomethyl)phenoxy]propyl}acetamide.

Among the compounds thus prepared 2-(trans-p-aminomethylcyclohexanecarboxy)-N-{3-[3-(1-piperidinomethyl)phenoxy] propyl}acetamide (hereinafter referred to as Compound RT) and 2-(N-carbobenzoxy-trans-p-aminomethylhexanecarboxy)-N-{3-[3-(1-piperidinomethyl)-phenoxy]propyl}acetamide (hereinafter referred to as Compound RTP) are preferable.

N-[3-(3-piperidinomethylphenoxy)propyl]hydroxyacetamide, which is an intermediate compound, is known as roxatidine. N-carbobenzoxyaminomethylhexanecarboxy chloride, which is another intermediate compound, is also a known compound. Both compounds can be prepared by known processes other than the above-described process.

The derivatives of the present invention can also be obtained by introducing appropriate groups by substitution at any appropriate stage in the synthesis of the compound of the present invention.

The above intermediate compounds dissolved in an organic solvent are stirred under ice cooling or at room temperature in the presence or absence of a catalyst to produce crystals, which is then collected by filtration. Triethylamine or the like is used as a catalyst. 2-(N-carbobenzoxy-trans-p-aminomethylhexanecarboxy)-N-{3-[3-(1-piperidinomethyl)phenoxy]propyl}acetamide of the present invention can be obtained by collecting the crystals. The crystals are dissolved into alcohol and catalytically hydrogenated in hydrogen gas in the presence of a catalyst to give 2-(aminomethylcyclohexanecarboxy)-N-{3-[3-(1-piperidinomethyl)phenoxy]-propyl}acetamide, which is another compound of the present invention. The catalytic hydrogenation is carried out at room temperature under atmospheric pressure using palladium-on-carbon as a catalyst. Isolation and purification of the target compound from the reaction mixture can be performed by means of conventionally known methods, such as separation by column chromatography, crystallization by vacuum concentration, and the like.

Figure 1:
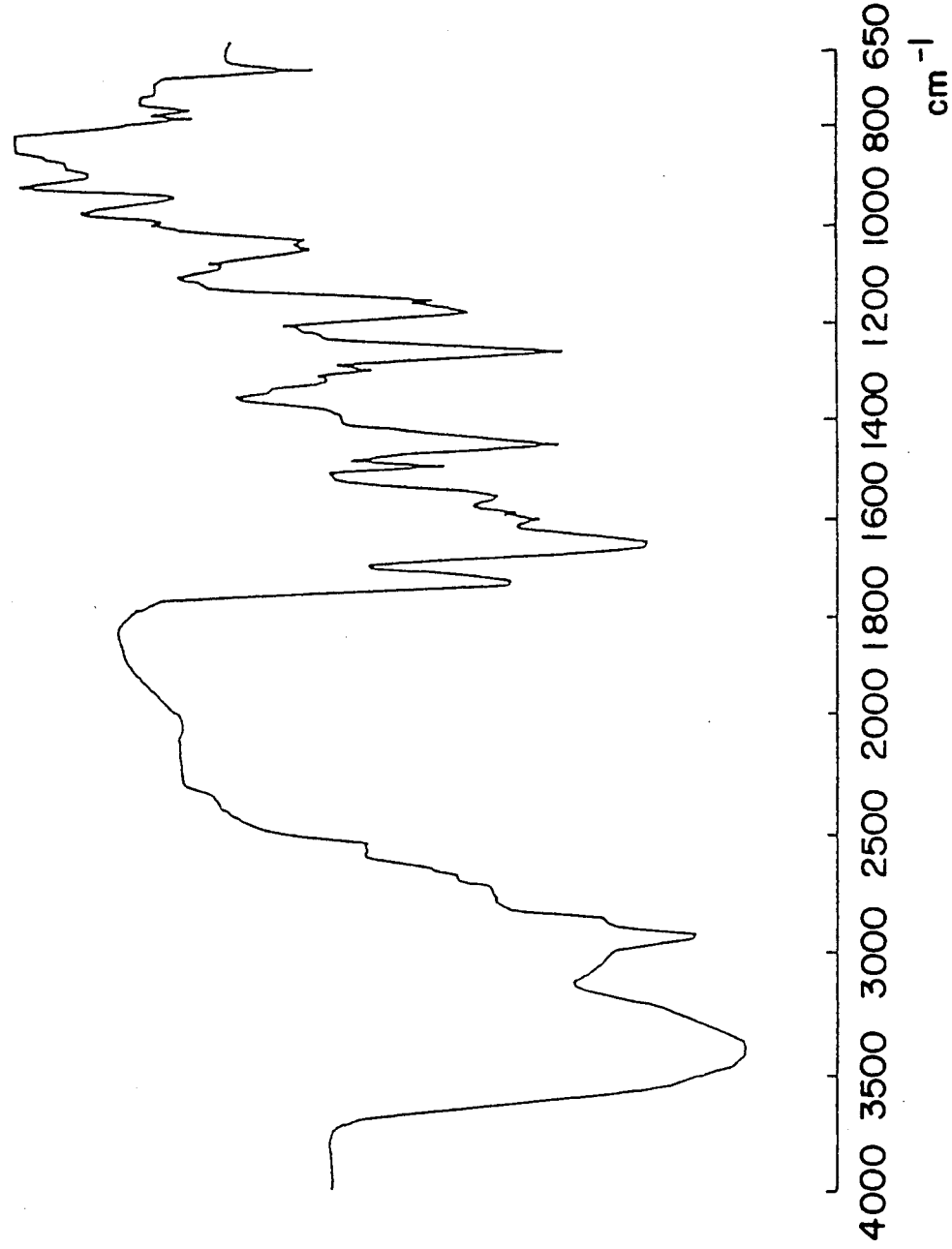
FIG. 1 is an IR spectrum (2R) of 2-(trans-p-aminomethylcyclohexanecarboxy)-N-{3-[3-(1-piperidinomethyl)phenoxy]propyl}acetamide, which is a compound of the present invention.
Figure 2:
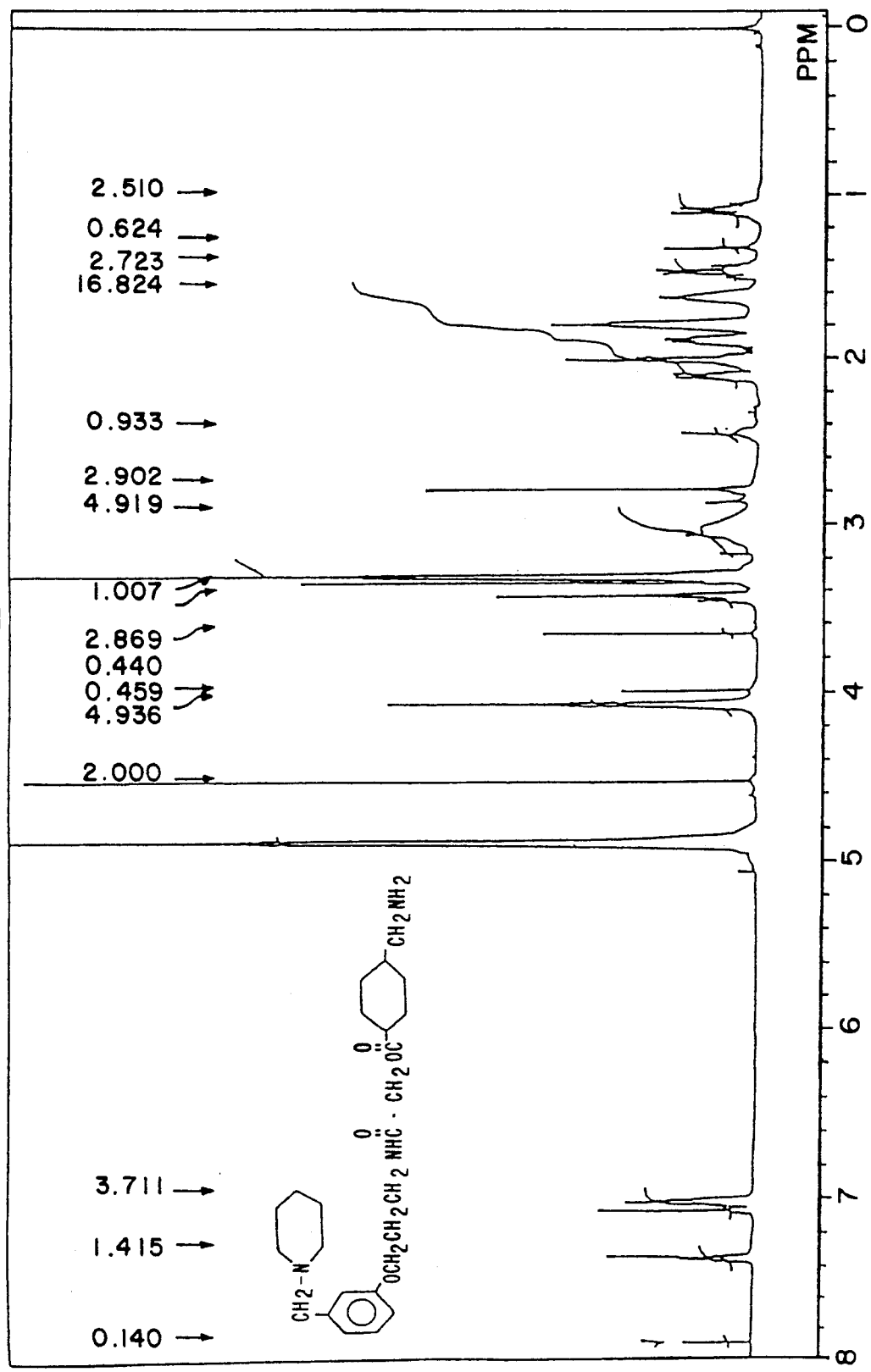
FIG. 2 is an NMR spectrum of the compound of FIG. 1.
Figure 3:
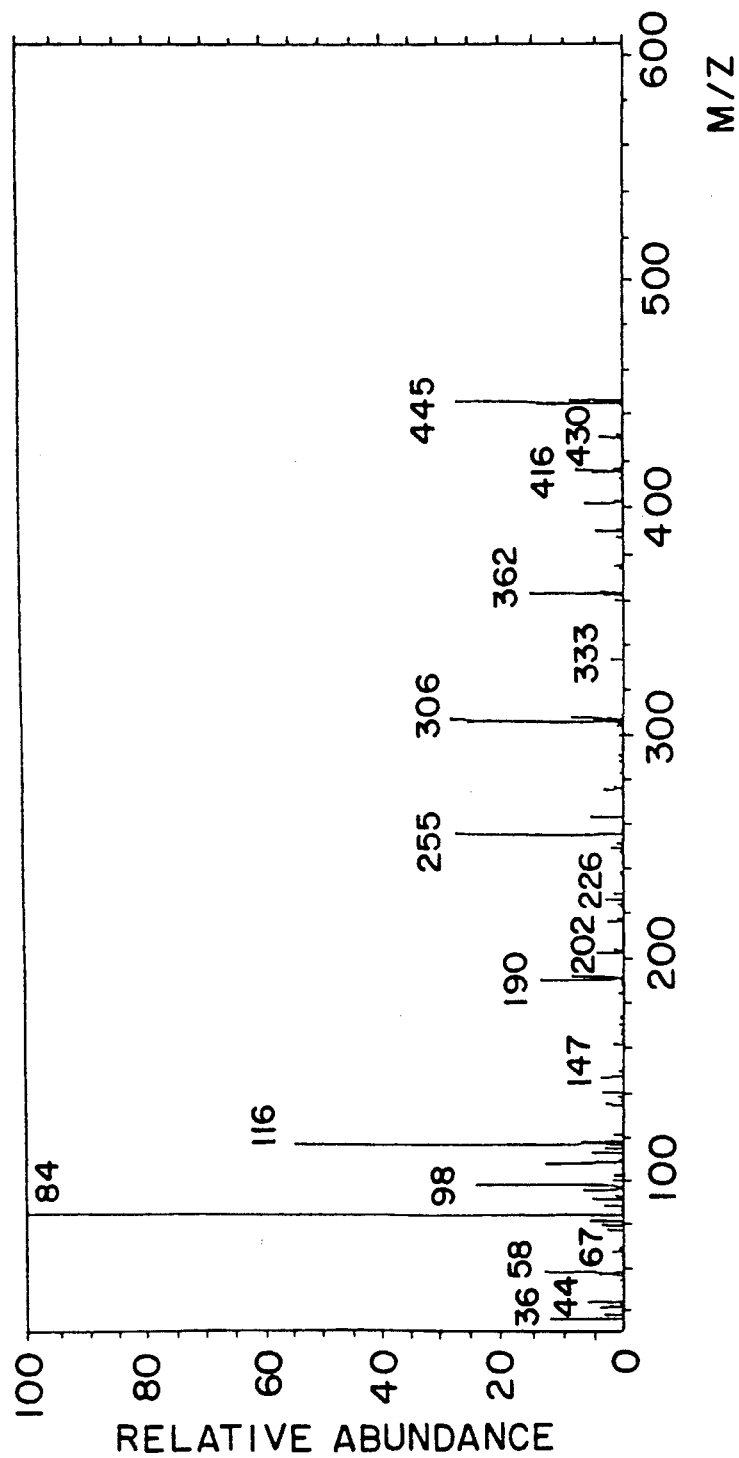
FIG. 3 is a mass spectrum of the compound of FIG. 1.
Figure 4:
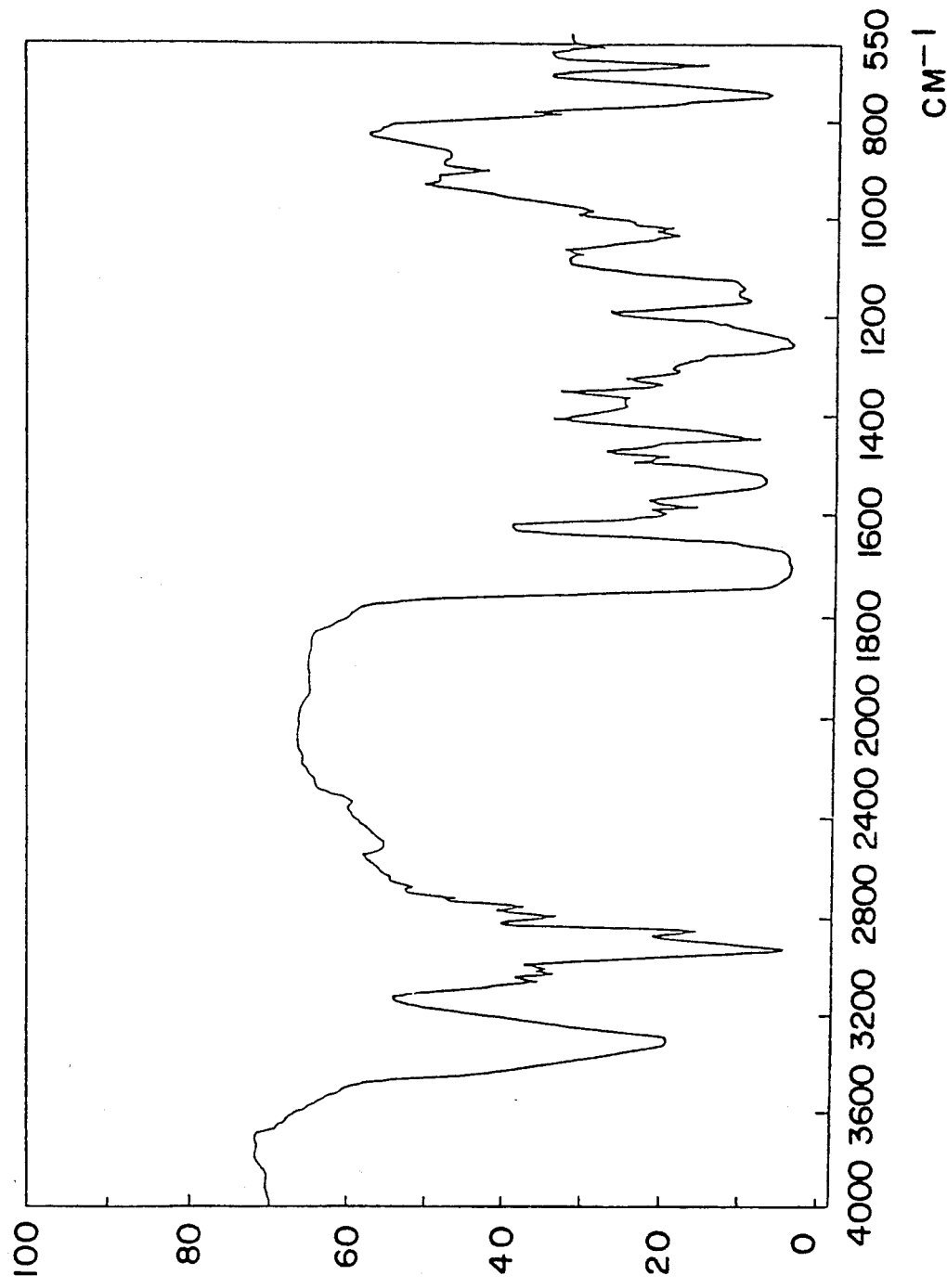
FIG. 4 is an IR spectrum (2R) of 2-(N-carbobenzoxy-trans-p-aminomethylhexanecarboxy)-N-{3-[3-(1-piperidinomethyl)phenoxy]propyl}acetamide, which is another compound of the present invention.
Figure 5:
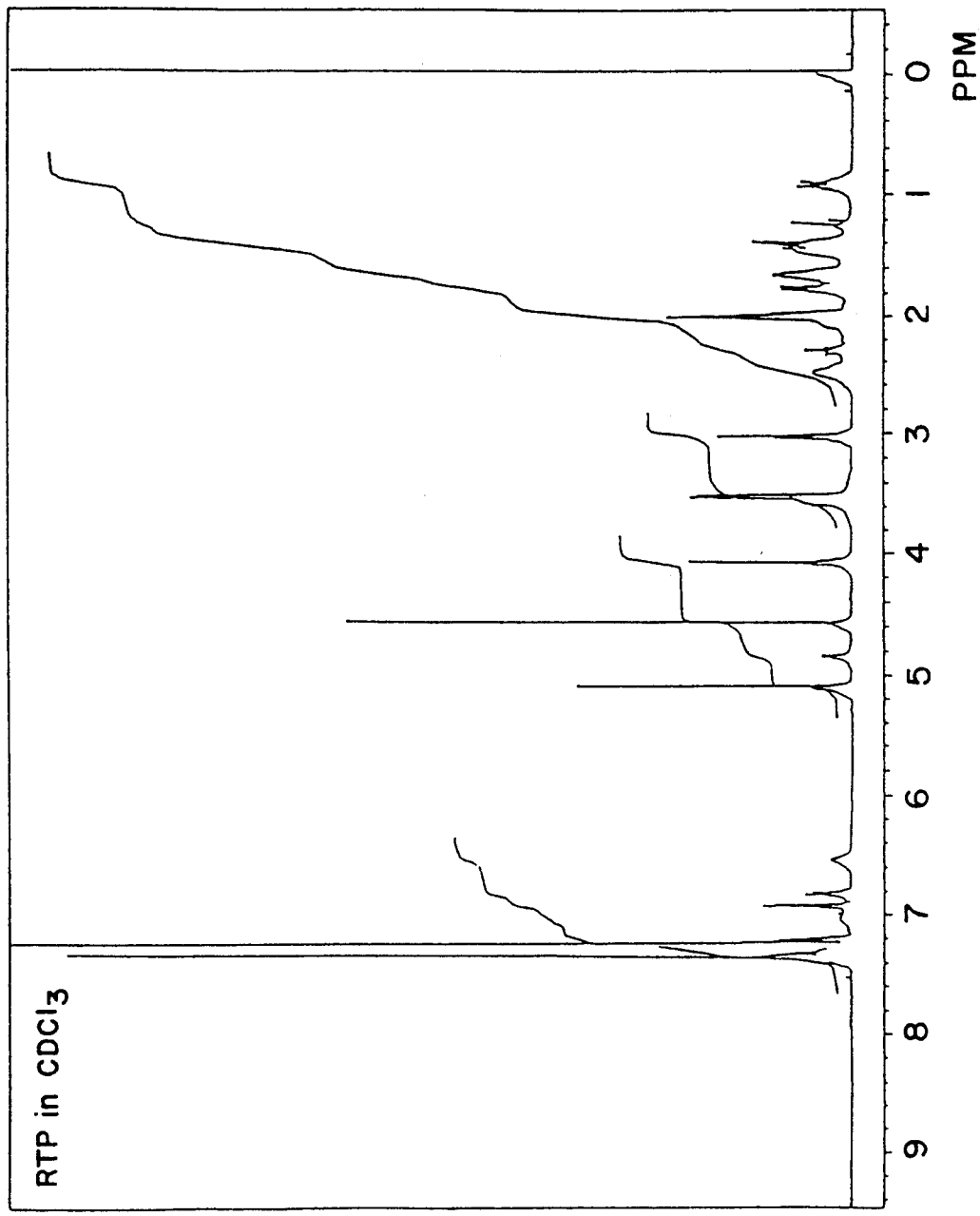
FIG. 5 is an NMR spectrum of the compound of FIG. 4.
Figure 6:
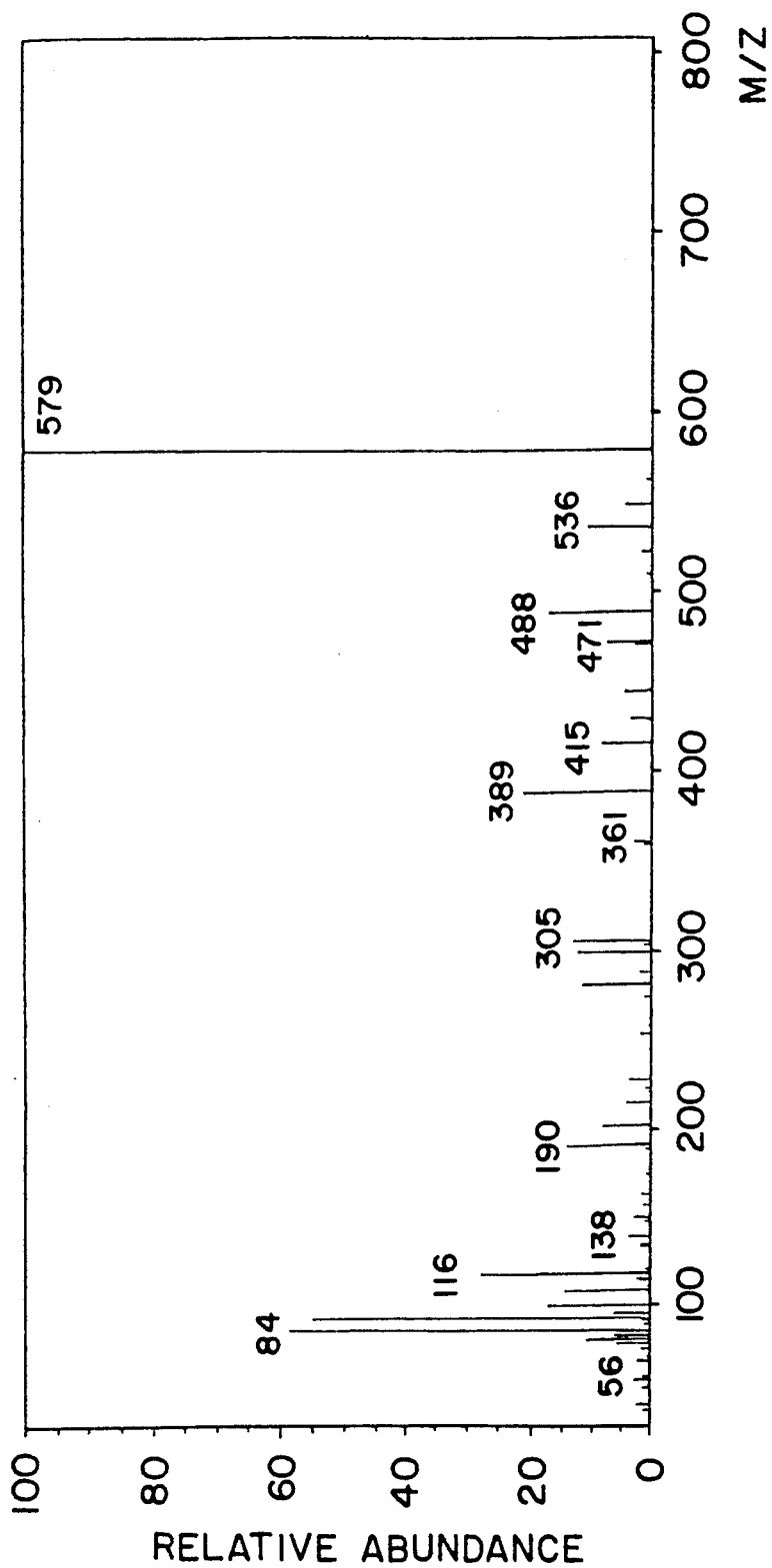
FIG. 6 is a mass spectrum of the compound of FIG. 4.

Regarding physicochemical characteristics of the compounds thus obtained, Compound RT is a light yellow or colorless oil and its IR, NMR and mass spectra are as shown in FIGS. 1–3; and Compound RTP is a light yellow paste and its IR, NMR and mass spectra are as shown in FIGS. 4–6.

Experiments on the suppression of ulcers induced by the water dipping stress and ulcers induced by hydrochloric acid-ethanol were carried out using rats to investigate the pharmacological activities of Compound RT and Compound RTP. The both compounds were found to effectively suppress the ulcers, confirming that the compounds of the present invention are useful as a drug, especially as an antiulcer drug.

Although a dose to humans varies depending on the symptoms, sex, age, and the like of the patients, all compounds of the present invention can cure ulcers induced by indigestion or stress, or can suppress their inducement, by administering them in an amount of 1-300 mg/day once a day or dividedly several times a day.

The compounds may be administered either orally or parenterally, even though oral administration is normally more preferred. Parenteral administration includes subcutaneous injection, intramuscular injection, intravenous injection, and, in cases, arterial injection.

The compound of the present invention may be formulated together with conventional carriers, disintegrators, lubricants, and the like, and formed into powders, granules, tablets, capsules, drinks, cataplasms, suppositories, or the like. Alternatively, it can be used as injection after dissolved into distilled water, physiological saline, or the like, followed by sterilization.

Other features of the invention will become apparent in the course of the following description of the exemplary embodiments which are given for illustration of the invention and are not intended to be limiting thereof.

EXAMPLES

EXAMPLE 1

Synthesis (1) Synthesis of 3-pyridinomethylphenol

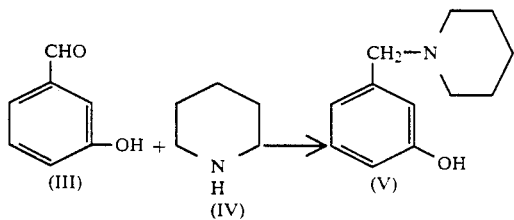

3-Hydroxybenzaldehyde (III) (0.246 mol, 30 g) was dissolved into 150 ml of methanol. Piperidine (IV) (0.6 mol, 52 g) was added to the solution and the mixture was stirred at room temperature to dissolution. To the solution was added under ice cooling sodium hydrogen borate (0.247 mol, 9.4 g) while stirring over 1 hour, followed by continued stirring for 1 hour at room temperature. The reaction mixture was concentrated under vacuum. The residue was dissolved in 200 ml of 3N hydrochloric acid and washed twice with 50 ml of ethyl acetate. The water layer was alkalinized (pH 10) with about 50 ml of concentrated aqueous ammonia to deposit crystals. The crystals were collected by filtration, washed with water, dried under vacuum, and recrystallized from a mixed solvent of acetone and n-hexane, to obtain 40 g of 3-piperidinomethylphenol (V) (yield: 84.7%). m.p. 135°-138° C.

(2) Synthesis of N-[3-(3-aminopropoxy)benzyl]piperidine

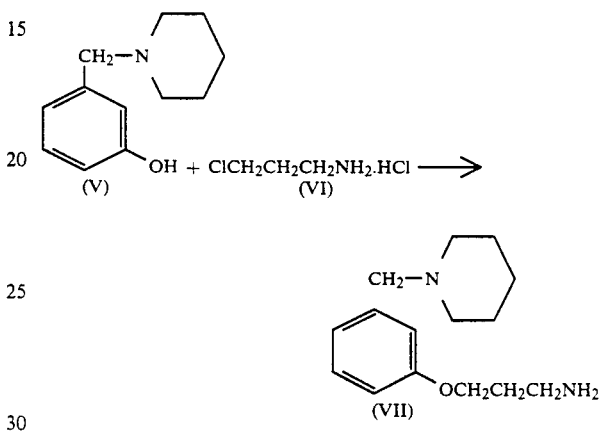

3-Chloropropylamine hydrochloride (VI) (0.2 mol, 39 g) was dissolved into 3N sodium hydroxide solution (containing 10% sodium chloride) and extracted with 300 ml of benzene. The benzene layer was dried over anhydrous magnesium sulfate. Separately, 3-piperidinomethylphenol (V) (0.2 mol, 38.2 g), sodium hydroxide (0.25 mol, 10 g), 100 ml of dimethylsulfoxide, and 70 ml of benzene were charged to a flask equipped with a water quantitative measurement tube, and heated at 130° C. for 3 hours while stirring to remove water produced by the tube, followed by continued stirring for 2 hours at 140°-150° C. To the resulting reaction mixture was dropwise added said benzene solution of 3-chloropropylamine at 150° C. while stirring over 4 hours. The reaction mixture was allowed to stand still to cool to room temperature to separate deposited sodium chloride by filtration. The filtrate was concentrated under reduced pressure and vacuum distilled to obtain 42.7 g of N-[3-(3-aminopropoxy)benzyl] piperidine (VII) (yield: 86.0%). m.p. 148°-151° C./0.25 mmHg.

(3) Synthesis of N-[3-(3-piperidinomethylphenoxy)-propyl]-hydroxyacetamide

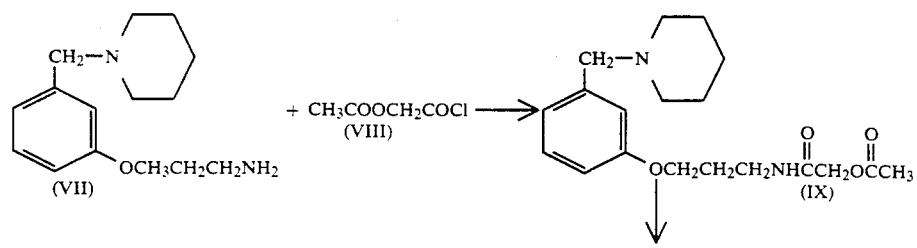

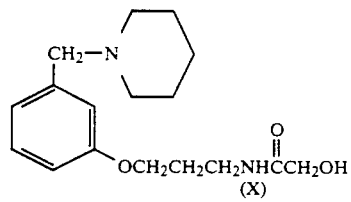

N-[3-(3-aminopropoxy)benzyl]piperidine (VII) (0.15 mol, 37.2 g) was dissolved into 200 ml of anhydrous benzene. To the solution was added triethylamine (0.18 mol, 18 g) and the mixture was stirred under ice cooling, followed by the dropwise addition of a solution of acetoxyacetyl chloride (VIII) (0.18 mol, 24.5 g) in 50 ml of dry benzene under ice cooling over 1 hour. After further stirring for 1 hour at room temperature, the deposited crystals of compound (IX) were separated by filtration. The filtrate was subjected to evaporation under reduced pressure, the residue was dissolved into 100 ml of 2N sodium hydroxide, and the solution was stirred for 5 hours at 50°-60° C. The resultant reaction mixture was extracted with dichloromethane, the extract was dried over anhydrous magnesium sulfate, and dichloromethane was evaporated under reduced pressure. The residue was purified by silica gel column chromatography (solvent: chloroform:methanol=10:1) to obtain 43.6 g (yield: 95%) of yellow oil of N-[3-(3-piperidinomethylphenoxy)propyl]hydroxyacetamide (X).

(4) Synthesis of N-carbobenzoxy-trans-p-aminomethylhexanecarboxy chloride

Tranexamic acid (XI) (0.25 mol, 39.3 g) was dissolved into 100 ml of 2N sodium hydroxide and the solution was stirred under ice cooling, following which carbobenzoxy chloride (XII) (0.3 mol, 51 g) was added dropwise over 1 hour. The mixture was allowed to become room temperature, followed by the addition of 5N hydrochloric acid to adjust the pH to 3. The resultant reaction mixture was extracted with 300 ml of dichloromethane, the extract was dried over anhydrous magnesium sulfate, and dichloromethane was evaporated under reduced pressure. 65 g of crystals of compound (XIII) obtained by recrystallization of the residue in chloroform was dissolved in 100 ml of anhydrous chloroform, and, after the addition of 50 ml of thionyl chloride, refluxed for 1.5 hours. The reaction mixture was distilled under reduced pressure and the residue was recrystallized in chloroform to obtain 54.4 g of N-carbobenzoxy-trans-p-aminomethylhexanecarboxy chloride (XIV) (yield: 80%). m.p. 79° C.

(5) Synthesis of 2-(N-carbobenzoxy-trans-p-aminomethylhexanecarboxy)-N-{3-[3-(1-piperidinomethyl)-phenoxy]propyl}acetamide (RTP)

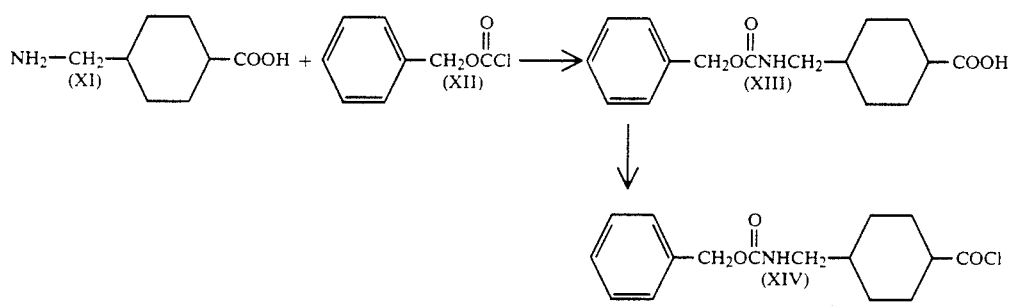

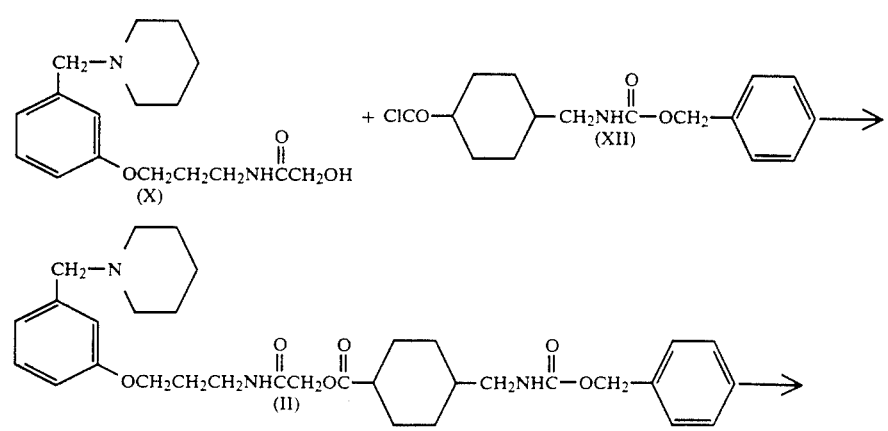

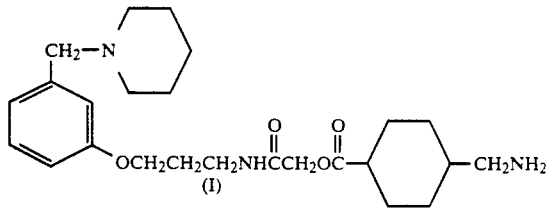

N-[3-(3-piperidinomethylphenoxy)propyl]hydroxyacetamide (X) (0.012 mol, 3.84 g) was dissolved into 100 ml of anhydrous benzene, and, after the addition of triethylamine (0.024 mol, 2.1 g), the mixture was stirred under ice cooling. 6.2 g (0.02 mol) of N-carbobenzoxy-trans-p-aminomethylhexanecarboxy chloride (XIV) dissolved in 100 ml of anhydrous benzene was added dropwise over 1 hour. The mixture was allowed to become room temperature and stirred for 30 minutes. The deposited crystals were collected by filtration to obtain 5.4 g (0.0094 mol) of light yellow paste of 2-(N-carbobenzoxy-trans-p-aminomethylhexanecarboxy)-N-{3-[3-(1-piperidinomethyl)phenoxy]propyl}acetamide (II). IR, NMR and mass spectra of the compound thus obtained are as shown in FIGS. 4-6. (6) Synthesis of 2-(trans-p-aminomethylcyclohexanecarboxy)-N-{3-[3-(1-piperidinomethyl)phenoxy]propyl}acetamide 2-(N-carbobenzoxy-trans-p-aminomethylhexanecarboxy)-N-{3-[3-(1-piperidinomethyl)phenoxy]propyl}acetamide (II) was dissolved into 10% palladium/carbon solution in ethanol and catalytically hydrogenated by hydrogen gas at room temperature under atmospheric pressure. Palladium/carbon was removed by filtration and the filtrate was evaporated under reduced pressure to obtain an oily product, which was developed on a thin layer chromatography plate using a chloroform-methanol (1:1) solvent as a developer. The spotted portion was scraped and extracted with methanol. The solvent was removed by evaporation under reduced pressure to obtain 2.5 g (0.0056 mol) of 2-(trans-p-aminomethylcyclohexanecarboxy)-N-{3-[3-(1-piperidinomethyl)phenoxy]propyl}acetamide as a light yellow or colorless oily substance (yield: 60%). IR, NMR and mass spectra of the compound thus obtained are as shown in FIGS. 1-3.

EXAMPLE 2

Pharmacological activity

Experiments were carried out to investigate the pharmacological activity of Compound RT using ulcer models in Wister male rats. Comparative tests were performed using commercial antiulcer drugs; Cetraxate (trade mark) and Roxatidine (trade mark), each having the following chemical structure.

Cetraxate:

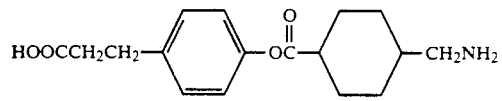

Roxatidine:

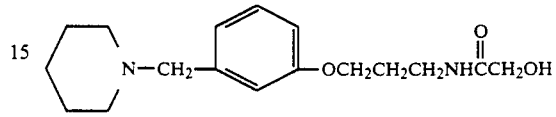

TABLE 1

| $ED_{50}$ values (mg/kg) in rat ulcer models | Cetraxate | Roxatidine |
|---|---|---|
| Hydrochloric acid-ethanol induced ulcer | 60 | 40 |
| Water immersion restrained stress induced model | 200 | 25 |

Water immersion restrained stress induced model

Groups of Wister male rats weighing 250-270 g, each group consisting of four rats, were fasted for 24 hours and subjected to the experiment. Cetraxate and Roxatidine, each suspended in 0.5% carboxymethyl cellulose (CMC), were administered to the rats using a per os probe, in an amount of 0.4 ml/100 g. 10 to 20 minutes after the administration, the animals were placed in an stress cage (manufactured by Natsume Manufacturing Co.) and dipped into water in a thermostat water bath at 21° C. to a depth of their processus xiphoideus to give a stress. After 7 hours, rats were taken out from the cage and sacrificed to cut out their stomach. 10 ml of a 2% formalin solution was charged into each stomach and the stomach was fixed in the solution for 10 minutes. After fixing, the stomach was opened along the greater curvature, and its mucosal surface was roughly washed with water. The length of hemorrhagic mucosal damages produced along the gastric gland was measured. The total of such length (mm) in each animal was taken as an index for the ulcer production. The ulcer suppression rate (%) was determined based on the index applying the following formula.

[(Ulcer index for the control)-(Ulcer index for the tested animal)]/(Ulcer index for the control)×100

The results are shown in Table 2.

TABLE 2

| Antiulcer activity of Compound RT in water immersion restrained stress induced model | | | |
|---|---|---|---|
| Drug | Dose (mg/kg) | Ulcer index (mm) | Suppression (%) |
| Control | | 10.3 ± 4.5 | |
| Compound RT | 36 | 0.7 ± 0.5 | 93.2 |
| Cetraxate | 25 | 6.0 ± 3.3 | 41.7 |
| Roxatidine | 25 | 2.5 ± 1.6 | 75.7 |

(2) Hydrochloric acid-ethanol induced ulcer

Groups of Wister male rats weighing 200-230 g, each group consisting of four rats, were fasted for 24 hours and subjected to the experiment. Cetraxate and Roxatidine, each suspended in 0.5% CMC, were administered to the rats using a per os probe, in an amount of 0.4 ml/100 g. 30 minutes after the administration, 1 ml (per rat) of 60% ethanol containing 150 mM HCl was administered using a per os probe at the same intervals as the test compound. After 1 hour, rats were sacrificed to cut out their stomach. 10 ml of a 2% formalin solution was charged into each stomach and the stomach was fixed in the solution for 10 minutes. After fixing, the stomach was opened along the greater curvature, and its mucosal surface was roughly washed with water. The length of hemorrhagic mucosal damages produced along the gastric gland was measured. The total of such length (mm) in each animal was taken as an index for the ulcer production. The ulcer suppression rate (%) was determined in the same manner as above.

The results are shown in Table 3.

TABLE 3

Antiulcer activity of Compound RT in hydrochloric acid-ethanol induced ulcer model

| Drug | Dose (mg/kg) | Ulcer index (mm) | Suppression (%) |
|---|---|---|---|
| Control | | 41.0 ± 10.9 | |
| Compound RT | 58 | 5.1 ± 5.5 | 87.6 |
| Cetraxate | 40 | 35.9 ± 14.7 | 12.5 |
| Roxatidine | 40 | 14.7 ± 9.9 | 64.2 |

In the both ulcer models, the novel compound RT of the present invention exhibited a lower ulcer index and a higher rate of suppression than Cetraxate and Roxatidine, indicating its high antiulcer activity.

(3) In order to more clearly identify the activity of Compound RT, both Roxatidine and Cetraxate hydrochloride were administered altogether. Since tranexamic acid is hardly absorbed by gastrointestinal tracts due to its abundant solubility in water, Cetraxate hydrochloride was used in its place. The experiments were performed by administering a dose corresponding to the $ED_{50}$ value of Roxatidine. The results are shown in Table 4 and 5.

TABLE 4

Antiulcer activity of Compound RT in hydrochloric acid-ethanol induced ulcer model

| Drug | Dose (mg/kg) | Ulcer index (mm) | Suppression (%) |
|---|---|---|---|
| Control | | 41.0 ± 10.9 | |
| Compound RT | 58 | 5.1 ± 5.5 | 87.6 |
| Cetraxate + Roxatidine | 40 | 4.9 ± 5.5 | 88.0 |

TABLE 5

Antiulcer activity of Compound RT in water immersion restrained stress induced model

| Drug | Dose (mg/kg) | Ulcer index (mm) | Suppression (%) |
|---|---|---|---|
| Control | | 10.3 ± 4.5 | |
| Compound RT | 36 | 0.7 ± 0.5 | 93.2 |
| Cetraxate + Roxatidine | 25 | 6.8 ± 2.5 | 66.5 |

As can be seen from the Tables, the activity of Compound RT against the hydrochloric acid-ethanol in-duced ulcer was almost the same as the case where both Roxatidine and Cetraxate hydrochloride were administered altogether. This is presumed the activities of Cetraxate hydrochloride and Roxatidine, having the $ED_{50}$ value of 60 mg/kg and 40 mg/kg, respectively, were exhibited synergistically to promote the same degree of effect as Compound RT. On the other hand, Compound RT exhibited a remarkably greater effect on the suppression of the acute gastroduodenal ulcer than the combined use of the two comparative drugs, demonstrating that its effect is not due to simple synergism.

EXAMPLE 3

10 g of Compound RT, 45 g of perfiller-101, 42 g of carboxymethyl cellulose, and 3 g of magnesium stearate were blended and made into granules according to a conventional method. The granules are orally administered in an amount of 1-3 g/day dividedly several times a day.

Obviously, numerous modifications and variations of the present invention are possible in light of the above teachings. It is therefore to be understood that within the scope of the appended claims, the invention may be practiced otherwise than as specifically described herein.

What is claimed is:

1. A drug composition for inhibiting secretion of gastric acid or protecting gastric mucosa comprising
   a. an effective amount of 2-substituted-N-{3-[3-(1-piperidinomethyl)phenoxy]propyl}acetamide, represented by the following formula,

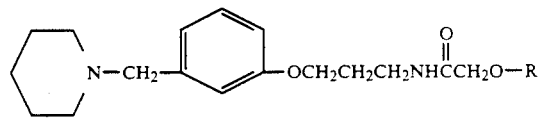

wherein R is an aminomethylcyclohexane carbonyl group,

or a pharmaceutically acceptable salt thereof; and
   b. a pharmaceutically acceptable carrier.

2. An antiulcer drug composition comprising an effective antiulcer amount of a compound selected from the group consisting of 2-(aminomethylcyclohexanecarboxy)-N-{3-[3-piperidino-methyl)phenoxy]propyl}acetamide of the following formula

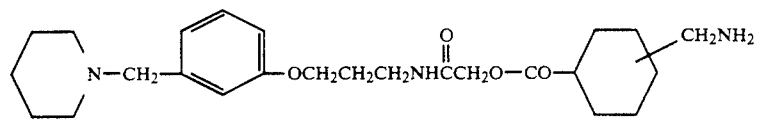

and pharmaceutically acceptable salts thereof and a pharmaceutically acceptable carrier.

3. The antiulcer drug composition of claim 2, wherein said acetamide compound is 2-(trans-p-amino-methyl-cyclohexanecarboxy)-N-{3-[3-(1-piperidinomethyl)-phenoxy]propyl}acetamide.

4. A composition comprising 2-(N-carbobenzoxy-aminomethylhexanecarboxy)-N-{3-[3-(1-piperidinomethyl(-phenoxy]propyl}acetamide, represented by the following formula

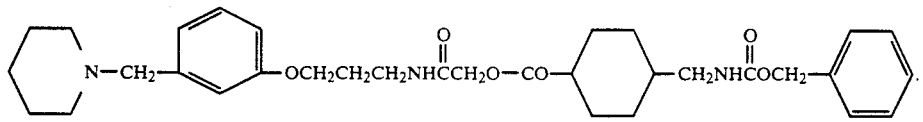

5. The composition of claim 4, wherein said acetamide compound is 2-(N-carbobenzoxy-trans-p-aminomethylhexanecarboxy)-N-{3-[3-(1-piperidino-methyl)-phenoxy]propyl}acetamide.

6. A composition for inhibiting secretion of gastric acid or protecting gastric mucosa in a patient comprising an effective amount of a compound selected from the group consisting of 2-substituted-N-{3-[3-(1-piperidinomethyl phenoxy]-propyl} acetamide, represented by the following formula

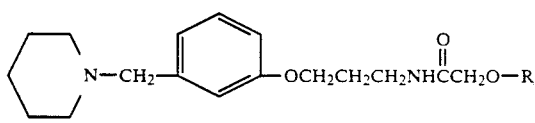

wherein R is an N-carbobenzoxy-aminomethyl-hexane carbonyl group and pharmaceutically acceptable salts thereof and a pharmaceutically acceptable carrier.

7. An antiulcer drug composition comprising an effective antiulcer amount of 2-(N-carbobenzoxyaminomethylhexane-carboxy-N-[3-{3-(1-piperidinomethyl)-phenoxy]propyl}acetamide represented by the following formula

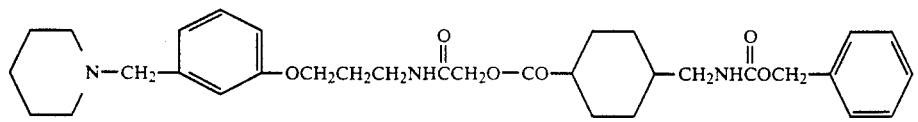

or a pharmaceutically acceptable salt thereof and a pharmaceutically acceptable carrier.

8. The drug composition of claim 7 wherein the acetamide compound is 2-(N-carbobenzoxy-trans-p-aminomethylhexane-carboxy)-N-[3-{3-(1-piperidinomethyl)-phenoxy]propyl}acetamide.

9. A method for inhibiting secretion of gastric acid or protecting gastric mucosa in a patient comprising administering to said patient a composition comprising an effective inhibitory or protective amount of a 2-(aminomethylcyclohexanecarboxy)-N-{3-[3-piperidinomethyl)phenoxy]propyl}acetamide compound represented by the formula:

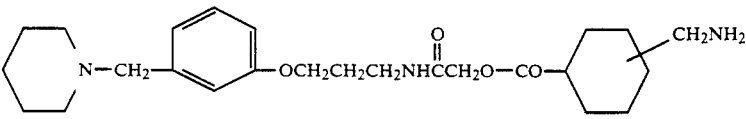

or a pharmaceutically acceptable salt thereof and a pharmacetically acceptable carrier.

10. The method of claim 9 wherein the acetamide compound is 2-(trans-p-aminomethylcyclohexanecarboxy(-N-{3-[3-piperidino-methyl)phenoxy]propyl-}acetamide.

11. A method for inhibiting secretion of gastric acid or protecting gastric mucosa in a patient comprising administering to said patient a composition comprising an effective inhibitory or protective amount of a 2-(N-carbobenzoxyaminomethylhexanecarboxy)-N-[3-{3-(1-piperidinomethyl)-phenoxy]propyl}acetamide compound represented by the formula:

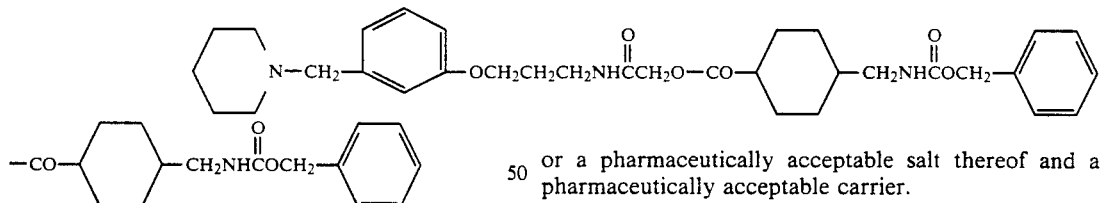

or a pharmaceutically acceptable salt thereof and a pharmaceutically acceptable carrier.

12. The method of claim 11 wherein the acetamide compound is 2-(N-carbobenzoxy-trans-p-aminomethyl-hexane-carboxy)-N-[3-{3-(1-piperidinomethyl)-phenoxy]propyl}acetamide.

13. A method for treating ulcers in a patient comprising administering to said patient a composition comprising an effective antiulcer amount of a 2-(aminomethyl-cyclohexanecarboxy)-N-{3-[3-piperidinomethyl)-phenoxy]propyl}acetamide compound represented by the formula:

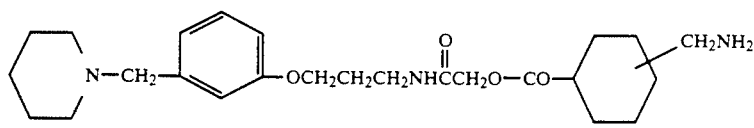

or a pharmaceutically acceptable salt thereof and a pharmaceutically acceptable carrier.

14. The method of claim 13 wherein the acetamide compound is 2-(trans-p-aminomethylcyclohexanecarboxy)-N-{3-[3-piperidino-methyl)phenoxy]propyl}acetamide.

15. A method for treating ulcers in a patient comprising administering to said patient a composition comprising an effective antiulcer amount of a 2-(N-carbobenzoxyaminomethylhexane-carboxy)-N-[3-{3-(1-piperidinomethyl)-phenoxy]propyl}acetamide compound represented by the formula:

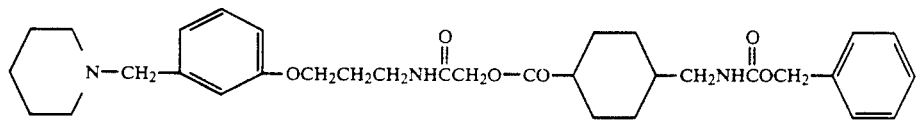

or a pharmaceutically acceptable salt thereof and a pharmaceutically acceptable carrier.

16. The method of claim 15 wherein the acetamide compound is 2-(N-carbobenzoxy-trans-p-aminomethylhexane-carboxy)-N-[3-{3(1-piperidinomethyl)-phenoxy]propyl}acetamide.

* * * * *

UNITED STATES PATENT AND TRADEMARK OFFICE
CERTIFICATE OF CORRECTION

PATENT NO. : 5,317,026
DATED : May 31, 1994
INVENTOR(S) : Masaki Otagiri and Teruko Imai It is certified that error appears in the above-indentified patent and that said Letters Patent is hereby corrected as shown below:

TITLE PAGE

[30]  Foreign Application Priority Data should read:

Feb. 23, 1993 [JP]  Japan.............5-057827
     Mar. 4, 1992 [JP]  Japan.............4-082864

Signed and Sealed this

Thirteenth Day of September, 1994

Attest:

BRUCE LEHMAN

*Attesting Officer*     *Commissioner of Patents and Trademarks*